United States Patent [19]

Lane et al.

[11] 3,998,218

[45] Dec. 21, 1976

[54] CHIROPRACTIC TABLE

[75] Inventors: Kenneth G. Lane, Ava; Emery J. Ropp, Seymour, both of Mo.

[73] Assignee: Kenneth G. Lane, Ava, Mo.

[22] Filed: Aug. 6, 1975

[21] Appl. No.: 602,281

[52] U.S. Cl. .......... 128/70

[51] Int. Cl.$^{2}$ .......... A61F 5/00

[58] Field of Search .......... 128/68–74; 269/322–328; 5/63–69

[56] References Cited

UNITED STATES PATENTS

| | | | |
|---|---|---|---|
| 2,244,758 | 6/1941 | Bell | 128/70 |
| 2,598,204 | 5/1952 | Allen | 128/74 |
| 2,631,300 | 3/1953 | Murray | 5/69 |
| 2,702,733 | 2/1955 | Lorang | 311/10 |
| 2,819,132 | 1/1958 | Rock | 311/10 |
| 2,926,660 | 3/1960 | Thompson | 128/70 |
| 3,092,102 | 6/1963 | Thompson | 128/70 |
| 3,282,584 | 11/1966 | Anderson | 269/325 |
| 3,312,985 | 4/1967 | Callaghan | 5/66 |
| 3,334,951 | 8/1967 | Douglass et al. | 269/328 X |
| 3,644,946 | 2/1972 | Swatt | 5/68 |
| 3,747,916 | 7/1973 | Benson | 269/322 |
| 3,795,018 | 3/1974 | Broaded | 5/68 |

*Primary Examiner*—Lawrence W. Trapp
*Attorney, Agent, or Firm*—Charles B. Cannon

[57] ABSTRACT

A chiropractic table which includes a supporting base and a sectional table supported thereby and comprised of a plurality of generally parallel separate table cushion sections or units which, for certain uses, are adapted to be disposed in generally coplanar horizontal alignment or relationship but are individually movable by the doctor into raised or elevated or lowered position and out of coplanar relationship relative to each other, for special purposes and treatments of the patient's spine by the doctor, and to adjust the height of the individual table cushion sections to the height of the doctor or his assistant. The new chiropractic table embodies manually controlled electrical switch means and electrical power means and power transmitting means for raising and lowering the individual table cushion sections separately and individually from either side of the table; foot operated switch means for simultaneously operating all of the electrical power means and all of the power transmitting means simultaneously from either side of the table to enable all of the table cushion sections to be raised and lowered simultaneously from either side of the table; and motion limiting means for limiting the extent of the upward and downward movement of the table cushion sections.

9 Claims, 16 Drawing Figures

CHIROPRACTIC TABLE

BACKGROUND OF THE INVENTION

Chiropractic tables have been known and used for many years and have included various forms of movable tables and table cushion sections, but none of them has had, insofar as we are aware, the versatility of our new table which enables the doctor or his assistant to raise or lower the individual cushion sections separately or simultaneously from either side of the table while treating the patient on the table, by means of manually operable switch control means arranged at each side of the table for selectively operating the electric power means and the power transmitting means for raising and lowering the individual table cushion sections from either side of the table and foot pedal operated switch control means for controlling the operation of the electric power means and the power transmitting means from either side of the table to enable all of the individual table cushion sections to be raised or lowered from either side of the table. Such earlier forms of chiropractic tables are disclosed in U.S. Pat. Nos. 2,702,733; 2,819,132; 2,926,660; 3,092,102 and 3,747,916 which illustrate various forms of manually or individually operated devices for raising and lowering one or more table cushion sections of a chiropractic table.

OBJECTS OF THE INVENTION

An object of the invention is to provide a new and improved chiropractic table which embodies a supporting base and a sectional table supported thereby and comprised of a plurality of horizontal separate table cushion sections which are generally parallel to each other and are adapted to be disposed in generally coplanar relationship for certain purposes and treatments of the patient by the doctor but are separately and individually movable into raised or lowered position and out of coplanar relationship relative to each other from either side of the table to enable the doctor to carry out certain treatments on the patient's spine and to adjust the table cushion sections to the height of the doctor or his assistant.

An additional object of the invention is to provide in the new chiropractic table a novel means for enabling the doctor or his assistant to raise or lower all of the table cushion sections simultaneously from either side of the table.

A further object of the invention is to provide in the new chiropractic table a novel combination and arrangement of electrical power means and power transmitting means for raising and lowering each of the table cushion sections and manually operable switch control means for the individual electrical power means to enable the doctor to readily move each of the table cushion sections separately into raised or lowered position and into and out of coplanar relationship relative to each other, from either side of the table, to enable the doctor to perform certain treatments on the patient's spine and to adjust the individual table cushion sections to the doctor's height or that of his assistant.

A further object of the invention is to provide a novel foot pedal operated switch control means for simultaneously controlling the operation of all of the electrical power means and power transmitting means from either side of the table to enable the doctor or his assistant to raise or lower all of the table cushion sections simultaneously from either side of the table.

An additional object of the invention is to provide in the new chiropractic table novel motion limiting means for limiting the extent of the upward and downward movement of the table cushion sections.

Other objects will appear hereinafter.

DESCRIPTION OF FIGURES IN THE DRAWINGS

Figure 1:
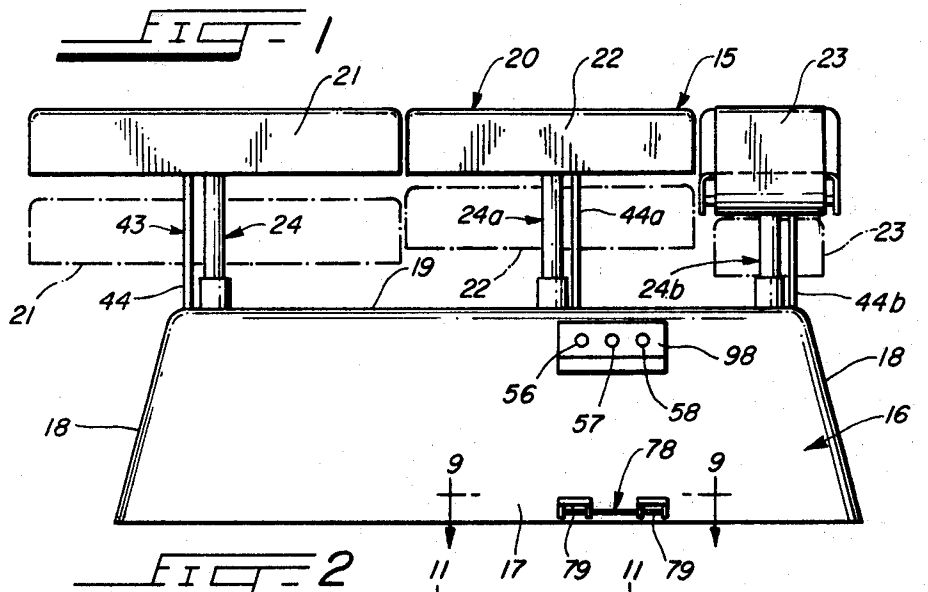
FIG. 1 is a side elevational view of a preferred embodiment of the new chiropractic table showing the individual table cushion sections in full lines in raised and coplanar relationship and showing them in dotted lines in lowered position and out of coplanar position.
Figure 2:
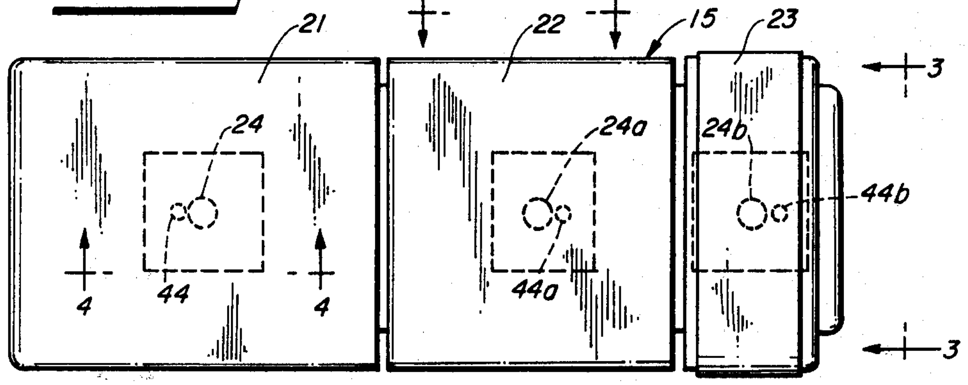
FIG. 2 is a top plan view of the chiropractic table shown in FIG. 1.
Figure 14:
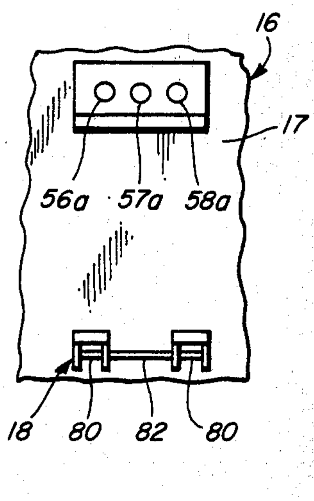
Figure 9:
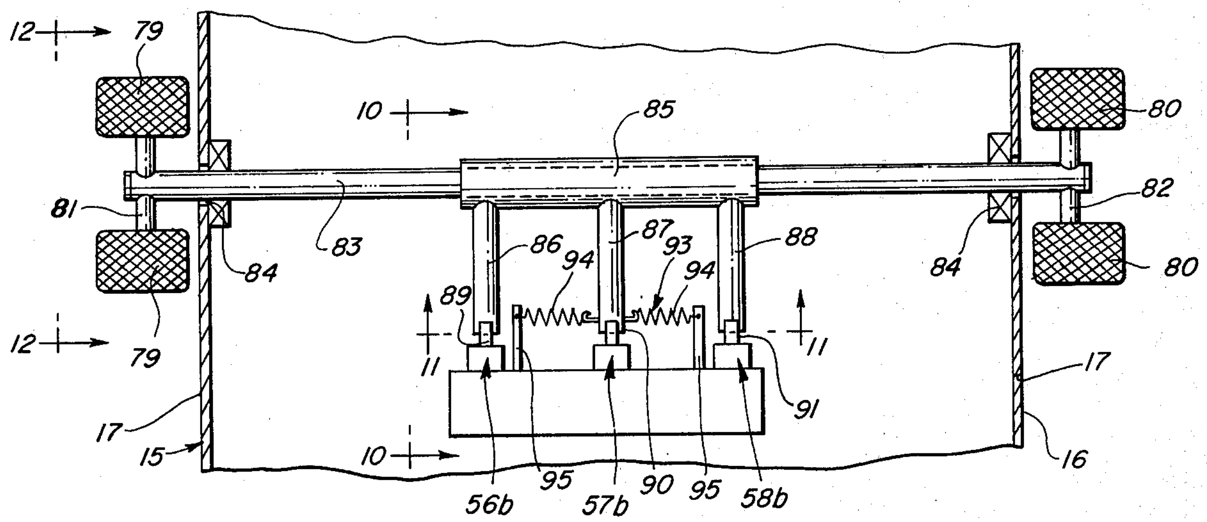
Figure 10:
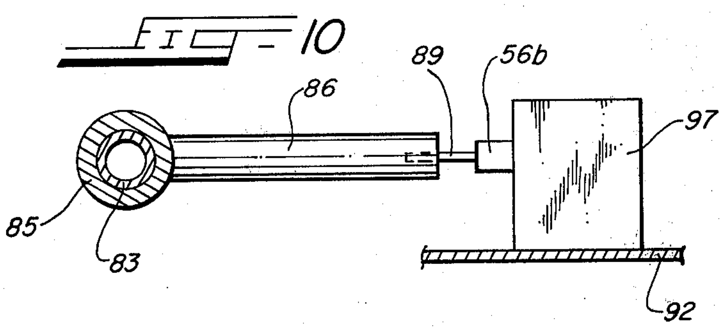
Figure 11:
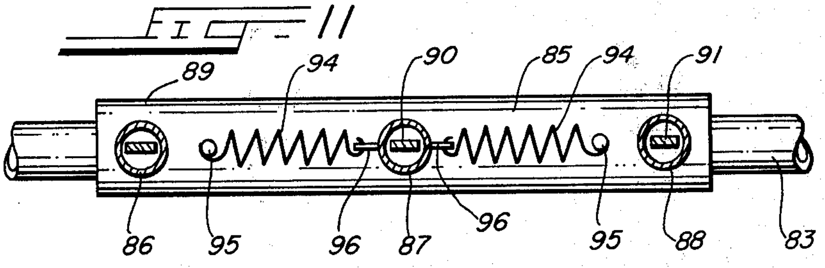
Figure 12:
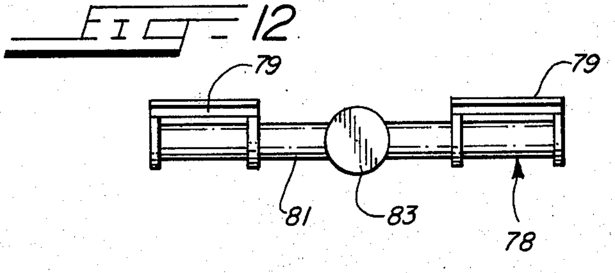
Figure 13:
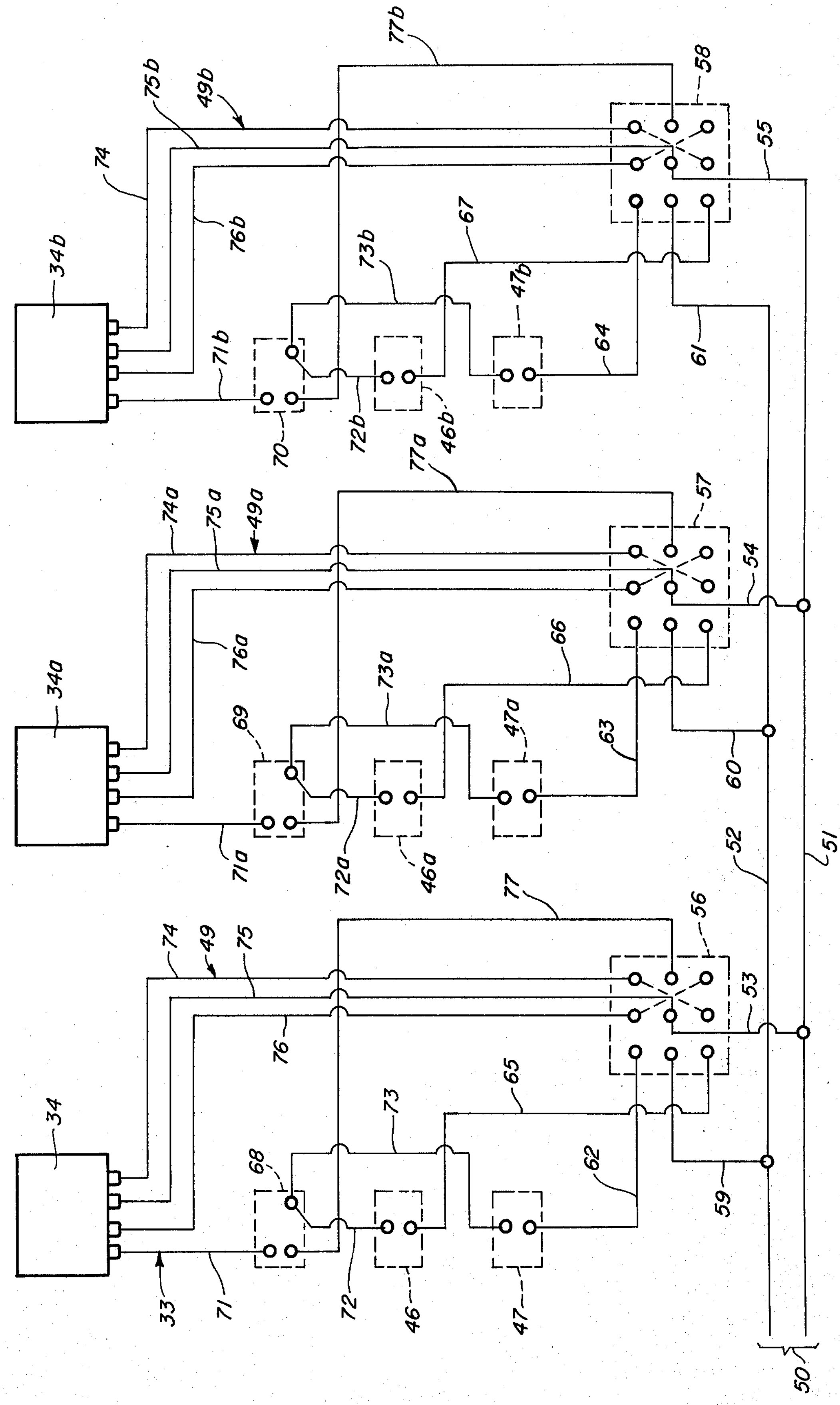
Figure 15:
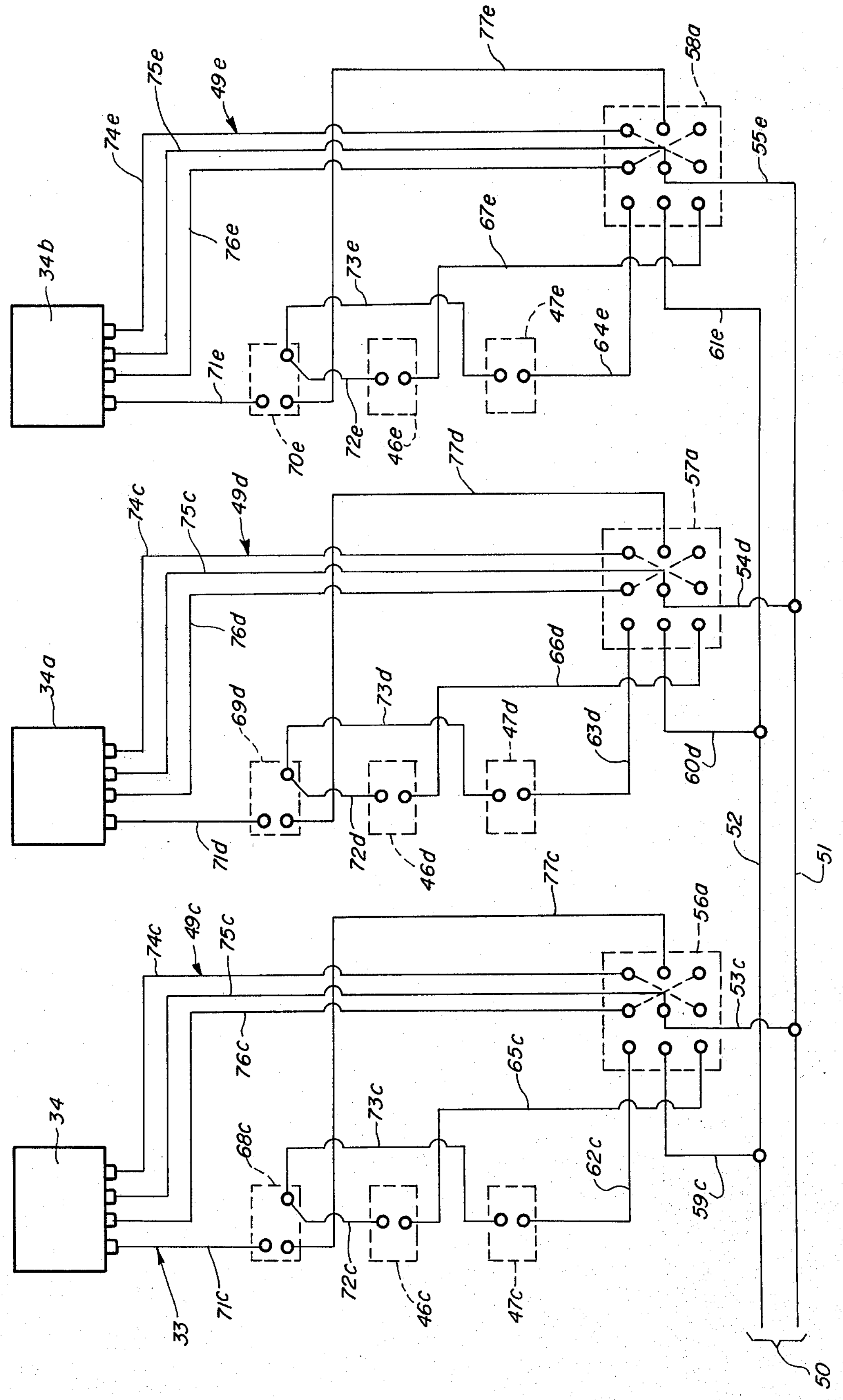
Figure 16:
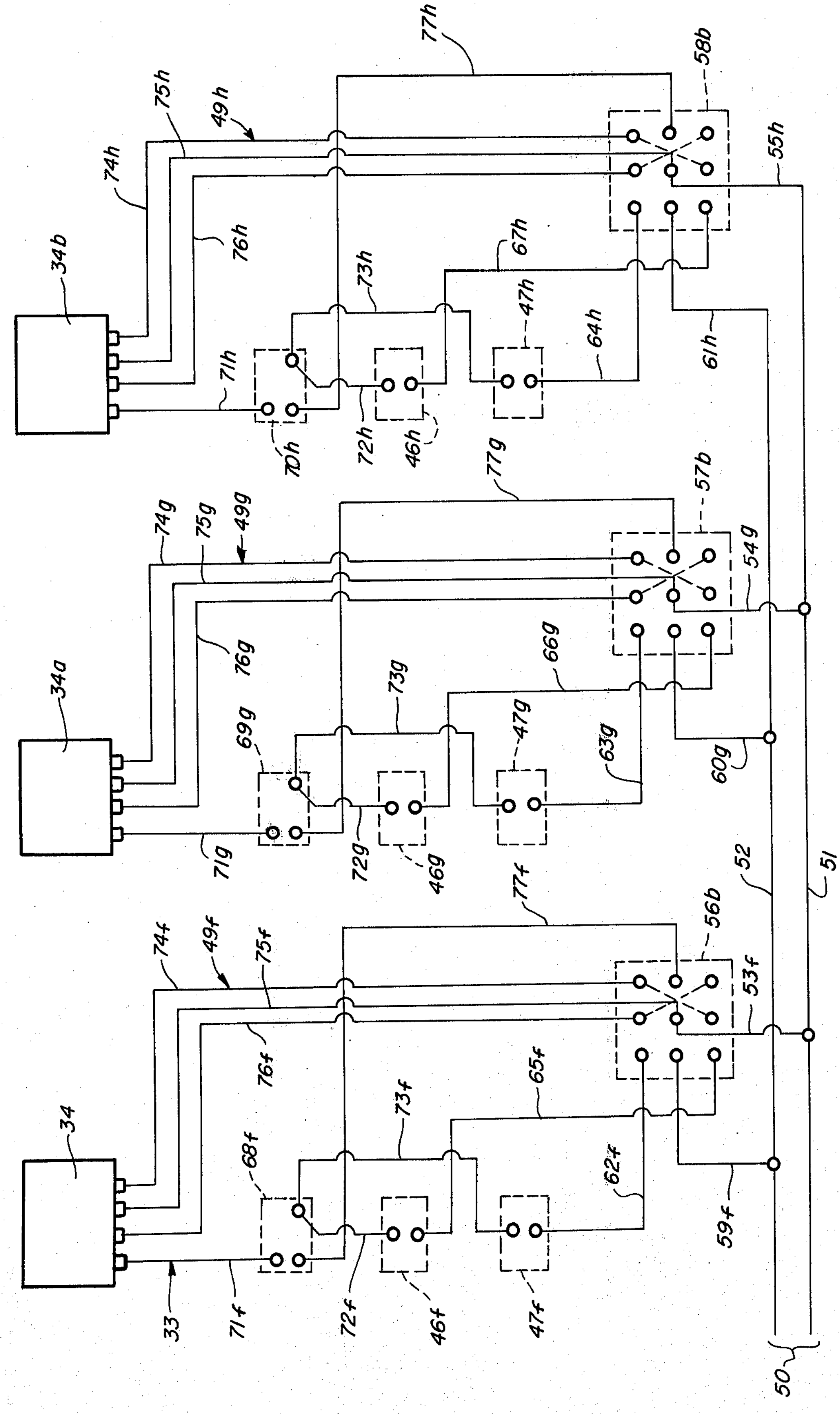

FIG. 9 is an enlarged sectional view illustrating the foot pedal operated switch control device which is embodied in the invention for simultaneously controlling the operation of all three electrical operating motors which are embodied in the invention from either side of the table to enable the doctor or his assistant to raise or lower all of the table cushion sections simultaneously from either side of the table;

FIG. 10 is an enlarged view on line 10—10 in FIG. 9, partly in section and partly in elevation;

FIG. 11 is an enlarged bottom sectional plan view on line 11—11 in FIG. 9;

FIG. 12 is an elevational view on line 12—12 in FIG. 9;

FIG. 13 is a schematic electrical circuit diagram illustrating a part of the electrical circuit embodied in the invention including the electrical power means in the form of the three reversible electrical operating motors which are embodied in the invention for operating the three individual table cushion sections and a first set of three manually operable toggle switch control means (FIG. 1) for individually operating the three electrical operating motors from one side of the table; and also showing the motion limiting control switches embodied in the invention for limiting the extent of the upward and downward movement of the table cushion sections; and illustrating schematically the directional current flow control devices one of which is embodied in each of the three electrical operating motors;

FIG. 14 is a fragmentary elevational view of the supporting base 16, as seen from the side opposite that shown in FIG. 1, and showing a second group of three manually operable toggle switches for manually controlling the operation of the three electrical operating motors which are embodied in the invention from the side of the table opposite the side shown in FIG. 1;

FIG. 15 is a schematic electrical circuit diagram similar to FIG. 13 but showing another part of the electrical circuit embodied in the invention for manually controlling the operation of the three electrical operating motors under the control of a second group of manually operable toggle switches (FIG. 14) from the side of the table opposite the side shown in FIG. 1; and FIG. 16 is a schematic electrical circuit diagram, similar to that shown in FIGS. 13 and 15, but showing that part of the electrical circuit which is under the control of the three foot pedal operated toggle switches shown in FIGS. 9, 10 and 11 for simultaneously operating all of the three electrical operating motors which are embodied in the invention from either side of the table under conrol of the foot pedal operated control device shown in FIGS. 9 to 12, inclusive.

DETAILED DESCRIPTION OF THE INVENTION AS ILLUSTRATED IN THE DRAWINGS

THE SECTIONAL CUSHION TABLE

A typical and preferred embodiment of the invention is illustrated in the drawings, wherein it is generally illustrated at 15, and comprises a generally rectangular-shaped hollow supporting base 16 which includes upwardly and inwardly angled or tapered side walls 17 and upwardly and inwardly angled or tapered end walls 18, and a generally horizontal top wall 19, and a table, generally indicated at 20, which is supported by and above the supporting base 16, and which includes a plurality of separately and simultaneously operable horizontally arranged upholstered frame table cushion sections 21, 22 and 23; the table cushion sections 21 and 22 being shown as generally square in form to provide a table for the body of the patient; and the head table cushion 23 being shown as being smaller than the body table cushion sections 21 and 22 and being generally rectangular in shape to provide a table cushion for the head of the patient, in use.

THE RAISING AND LOWERING MEANS FOR THE INDIVIDUAL TABLE CUSHION SECTIONS 21-22-23

The present invention embodies individual raising and lowering means, generally indicated at 24, 24*a* and 24*b*, for separately raising and lowering each of the individual table cushion sections 21, 22 and 23, individually or simultaneously, and since these raising and lowering means 24, 24*a* and 24*b* are all of the same construction, only one of them will be described in detail, namely, the raising and lowering means 24 for the table cushion section 21; the corresponding parts in the other individual raising and lowering means being indicated by the same reference numerals followed by the additional reference characters *a* and *b*.

Figure 4:
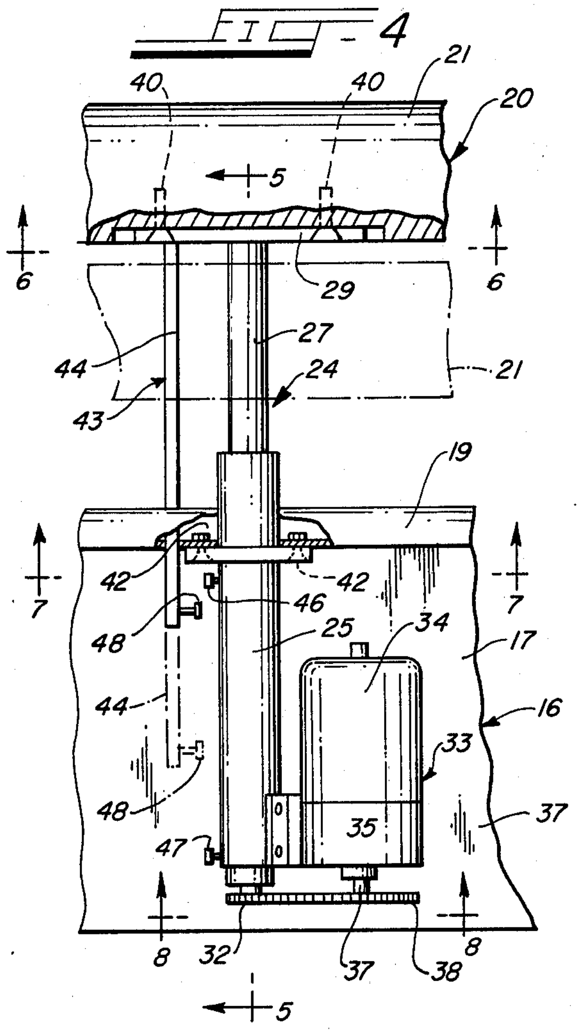
FIG. 4 is an enlarged sectional view on line 4—4 in FIG. 2, showing the individual raising and lowering means for one of the individual table cushion sections; the electrical power means for the said one of the individual table cushion sections; and the power transmitting means associated with the said electrical power means; and related parts.
Figure 5:
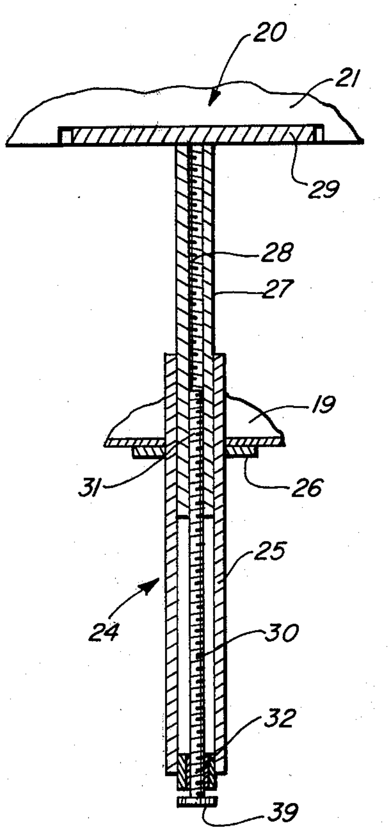
FIG. 5 is a central vertical sectional view on line 5—5 in FIG. 4 showing the individual raising and lowering means for one of the individual table cushion sections.
Figure 6:
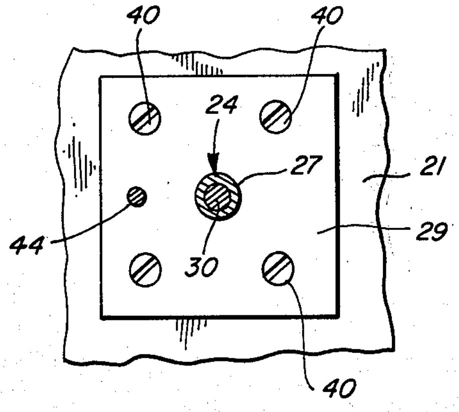
FIG. 6 is a bottom sectional plan view on line 6—6 in FIG. 4.
Figure 7:
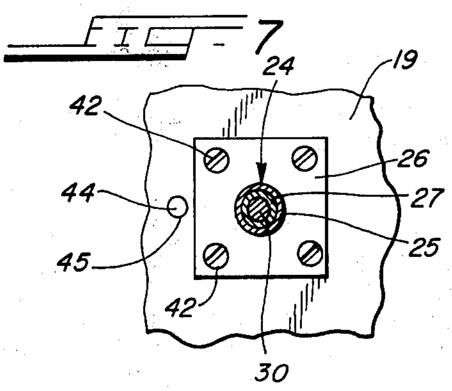
FIG. 7 is a bottom sectional view on line 7—7 in FIG. 4.

As shown in FIGS. 4, 5, 6 and 7 the raising and lowering means 24 includes a stationary jack housing in the form of a vertical tubular member 25 which is rigidly mounted in and extends upwardly through the top wall 19 of the hollow supporting base 16 to which it is rigidly attached in any suitable manner, as by a mounting plate 26 which is attached to the top wall 19 of the supporting base 16 as by screws 42 (FIGS. 5 and 7). A second and smaller movable tubular member 27 is arranged within and is movable within the larger tubular member or stationary jack housing 25 and is internally screw threaded, as at 28 (FIG. 5) for the reception of an externally threaded screw member 30 which extends upwardly through the outer and larger tubular member or jack housing 25 and has an upper end portion, as 31, which works in the internally screw threaded tubular member 27 (FIG. 7). The internally threaded screw member 27–28 has a horizontal and generally square platform 29 attached thereto at its upper end, as by fastening elements in the form of screws 40, and the screw member 31 has a lower end portion 32 which projects downwardly below the outer tubular member or jack housing 25, as shown in FIG. 5.

THE MOTION LIMITING CONTROL SWITCH MEANS FOR THE TABLE CUSHION SECTION RAISING AND LOWERING MEANS

The present invention includes motion limiting control switch means for each of the raising and lowering devices 24–24*a*–24*b*, but since these motion limiting control switch means are all of the same construction only one of the same will be described, namely, the motion limiting control switch means for the raising and lowering means 24 which is generally indicated at 43 (FIGS. 1, 4, 6 and 7) and includes actuating means for the motion limiting control switches, which will be described hereinafter, and which actuating means includes a vertically extending motion limiting control rod member 44 which is slidably mounted in and is guided in an opening 45 in the top wall 19 of the supporting base 16 and has an upper end portion which is anchored in and is suspended from the plate 29 at the bottom of the table cushion section 21 (FIGS. 4 and 7).

A first motion limiting control switch 46 is mounted on the outer surface of the upper end portion of the outer tubular member or jack housing 25 and a second motion limiting control switch 47 is mounted on the outer surface of the lower end portion of the tubular member or jack housing 25 (FIG. 4). The actuating means for the motion limiting control switches 46 and 47 includes a striker arm member 48 which is mounted on the lower end portion of the motion limiting control rod member 46 and faces toward the outer tubular member or jack housing 25 (FIG. 4).

The operation of the motion limiting control switch means 43 will be described in detail in connection with the detailed description of the invention and the electrical power supply and control circuits which are embodied in the invention, as shown in FIGS. 13, 15 and 16, and which will be described hereinafter.

THE ELECTRICAL POWER MEANS, ELECTRICAL POWER SUPPLY MEANS, AND THE POWER TRANSMITTING MEANS FOR OPERATING THE RAISING AND LOWERING MEANS FOR THE TABLE CUSHION SECTIONS

The present invention embodies individual electrical power means and electrical power supply means for operating each of the raising and lowering means 24, 24*a* and 24*b* for the table cushion sections 21–22–23, individually or simultaneously, and such individual electrical power means and electrical power supply means is generally indicated at 33 (FIGS. 4, 13, 15 and 16) and includes a plurality, namely, three reversible electrical operating motors 34–34*a*–34*b* each of which is suitably mounted in the supporting base 16, as by being attached by a bracket 35 to the outer tubular member or jack housing 25 (FIG. 4).

Figure 8:
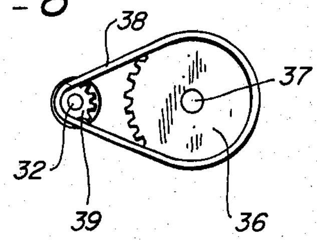
FIG. 8 is a bottom sectional plan view on line 8—8 in FIG. 4.

The power transmitting means for each of the raising and lowering means 24–24*a*–24*b* includes a sprocket gear 36 which is attached to the lower end portion 37 of the drive shaft of each of the electrical motors 34–34a–34b, and a sprocket chain, as 38, which works around each of the sprocket gears, as 36, and around a smaller sprocket gear, as 39, which is attached to the lower end portion, as 32, of each of the jack screw members, as 30 (FIGS. 4 and 8).

THE ELECTRICAL POWER SUPPLY AND CONTROL CIRCUITS FOR THE REVERSIBLE ELECTRICAL OPERATING MOTORS 34–34a–34b AND FOR THE MOTION LIMITING SWITCH CONTROLS 46–47, 46a–47a AND 46b–47b (FIGS. 13, 15 AND 16) AND RELATED PARTS

The electrical power supply and control circuits for the three reversible electrical operating motors 34–34a–34b and for the motion limiting control switches 46–47, 46a–47a and 46b–47b, and related parts, are shown schematically in FIGS. 13, 15 and 16 and are generally indicated at 49–49a–49b.

Thus, referring to FIG. 13, the electrical power supply and control circuits 49–49a–49b include a power source 50 which includes power inlet lines, as 51–52, which are suitably grounded, and lead by way of lines 53–54–55 to one side of the three motor control toggle switches 56, 57 and 58, respectively (FIGS. 1 and 13).

The present invention embodies a total of nine (9) toggle switches but only three (3) of them, namely, the toggle switches 56–57–58 are shown in FIG. 13, the other six toggle switches being shown in FIGS. 15 and 16, as will be described hereinafter. The nine toggle switches are arranged in groups of three (3). Thus, one (1) group of three (3) of the toggle switches, namely, the group consisting of the three (3) toggle switches 56–57–58 (FIGS. 1 and 13) are manually operable toggle switches and are arranged on one side of the supporting base 16, as shown in FIG. 1, within a control box 98 (FIG. 13) for manual operation from the side of the table 15 shown in FIG. 1. Similarly, a second group of three (3) manually operable toggle switches 56a–57a–58a are arranged on the side of the supporting base 16 opposite the side shown in FIG. 1, as shown in FIG. 14, within a control box, 98a, and the third group of toggle switches 56a–57a–58a are arranged within the supporting base 16 (FIGS. 9, 10 and 11) and within a control box, 97, (FIG. 10) for simultaneous operation from either side of the table 15 by a foot pedal operated switch control device 78 (FIGS. 9 to 12, inclusive) which will be described hereinafter. Thus, the two groups of three manually operable toggle switches 56–57–58 and 56a–57a–58a provide for individual manual control and operation of the three reversible electrical operating motors 34–34a–34b from either side of the table 15 whereas the third group of toggle switches 56b–57b–58b provide for simultaneous operation of all three of the electrical operating motors 34–34a–34b from either side of the table 15 under the control of the foot pedal operated switch control device 78 FIGS. 9 to 12, inclusive) which will be described hereinafter.

The toggle switches 56–57–58, 56a–57a–58a and 56b–57b–58b are all of the same type and construction and the electrical circuit and wiring arrangement for each of them is substantially the same, and is as shown in FIGS. 13, 15 and 16. Thus, a suitable toggle switch for use in the present invention is one manufactured and sold by Dayton Electric Manufacturing Company, 5959 West Howard Street, Chicago, Illinois 60648 and is known as a three pole double throw center off motor reversing switch (4 inches × 8 inches × 7 inches) and is identified as its Model No. 4X814.

Power control lines 59–60–61 lead from the power intake lines 51–52 to the other side of the manually operable motor control toggle switches 56–57–58, respectively. Power intake lines 62–63 lead from the motor control toggle switches 56–57 and 58, respectively, to the lower motion limiting control switches 47–47a–47b, respectively, and power intake lines 65–66 and 67 lead from the manually operable motor control toggle switches 56–57 and 58, respectively, to the upper motion limiting control switches 46–46a–46b, respectively. Directional current control devices 68–69–70 are embodied in each of the three reversible electrical motor operating motors 34–34a–34b but for the purpose of simplicity and explanation these directional current flow control devices 68–69–70 are shown in the drawings (FIGS. 13, 15 and 16) as being arranged outside of the reversible motors 34–34a–34b but in the motor control circuits 49–49a–49b, respectively, between the upper motion limiting control switches 46–46a–46b and the electrical operating motors 34–34a–34b, respectively, to control the direction of rotation of the three (3) electrical operating motors 34–34a–34b.

An electrical conductor line 71 is shown as leading from one side of the directional current flow control device 68 to the electrical operating motor 34, and similar electrical conductor lines 71a and 71b are, for the purpose of simplicity in explanation, shown as leading from the directional current flow control devices 69 and 70 to the operating motors 34a and 34b, respectively (FIG. 13).

A line 72 leads from one side of the upper motion limiting control switch 46 to the directional current flow control device 68; and similar lines 72a and 72b lead from one side of each of the directional current flow conrol devices 69 and 70 to the upper motion limiting control switches 46a and 46b, respectively (FIG. 13).

A line 73 leads from one side of the lower motion limiting control switch 47 to the directional current flow control device 68 and similar lines 73a and 73b are shown as leading from the motion limiting control switches 47a and 47b to the directional current flow control device 69 and 70, respectively (FIG. 13).

Lines 74–75 and 76 lead from the toggle switch 56 to the operating motor 34 and similar lines 74a and 74b, respectively, lead from the toggle switches 57 and 58 to the operating motors 34a and 34b, respectively (FIG. 13).

An electrical conductor line 77 is shown as leading from the toggle switch 56 to the directional current flow control device 68 and similar electrical conductor lines 77a and 77b lead from the toggle switches 57 and 58 to the electrical operating motors 34a and 34b, respectively (FIG. 13).

THE FOOT PEDAL OPERATED TOGGLE SWITCH CONTROL DEVICES (FIGS. 9 TO 12, INCLUSIVE)

Figure 3:
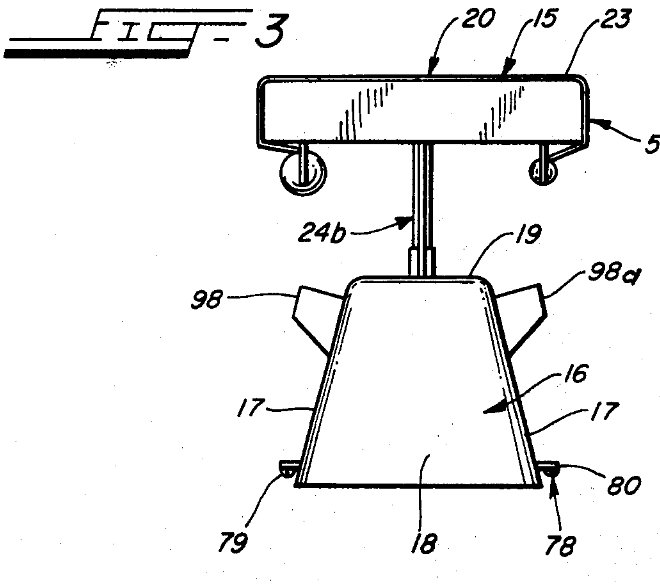
FIG. 3 is an end elevational view on line 3—3 in FIG. 2.

The present invention provides a foot pedal controlled or operated device for simultaneously controlling the operation of the third group of three toggle switches 56b–57b–58b. This foot pedal operated switch control device is shown in FIGS. 9 to 12, inclusive, wherein it is generally indicated at 68, and includes two pairs of rubber or like resilient foot pedal members or pads 79—79 and 80—80, one pair of which is mounted on each side of the table 15 adjacent the bottom of the supporting base 16 (FIGS. 3 and 9). These rubber or like resilient foot pedal members or pads 79—79 and 80—80 are mounted on supporting arms 81 and 82, respectively (FIG. 9) which, in turn, are mounted on a horizontally extending supporting rod or rock shaft 83 which is rotatably mounted in openings 84 which are provided in the side walls 17 of the supporting base 16 (FIG. 9).

A tubular sleeve 85 is mounted in and is fixed to the horizontally extending supporting rod or rock shaft 83 midway between the ends thereof and within the supporting base 16 of the table 15, and three generally vertically extending tubular toggle switch operating members 86, 87 and 88 are mounted on and have their upper end portions fastened to the tubular sleeve 85 in spaced relationship thereon (FIG. 9).

Each of the tubular toggle switch operating members 86, 87 and 88 has an open lower end and the upper end portions of the movable toggle switch operating arms or members 89–90 and 91 project into the open lower ends of the tubular switch operating members 86, 87 and 88, respectively, of the toggle switches **56*b*–57*b*–58*b*, which are mounted in spaced relationship in a control box 97, on a supporting plate member 92 which is mounted on the supporting frame of the table 15 within the supporting base 16 (FIGS. 9 and 10**).

The present invention includes a resetting means for the three foot pedal controlled toggle switches **56*b*–57*b*–58*b*, which is generally indicated at 93 (FIGS. 9 and 11), and includes a pair of resetting coil springs 94 each of which has an outer end portion attached to the upper end portion of an upright supporting member 95 which is mounted on the supporting plate or member 92, and each of these resetting coil springs has an inner end portion attached, as at 96, to the center tubular toggle switch operating member 87 FIGS. 9 and 11**).

MISCELLANEOUS CHARACTERISTICS AND FEATURES

The raising and lowering jack devices **24–24*a*–24*b* are preferably in the order of two (2) ton capacity; the speed of vertical movement of the raising and lowering of the jack devices 24–24*a*–24*b* and of the table cushion sections 21–22–23 supported thereby, is preferably in the order of one (1) inch per second; and the reversible electrical operating motors 34–34*a*–34*b*** are preferably one sixth (1/6) horsepower split phase four (4) pole, 3 amp., 115 volt, torque 65 lbs., in line heavy duty full load reversible fully enclosed gear motors, operating at a preferred speed of 135 rpm (Dayton Electric Company, Stock No. 6K334).

The directional current flow control devices, as 68–69–70 (FIG. 13) are, as pointed out above, built into the reversible electric motors **34–34*a*–34*b* but, for the purpose of explanation of the operating circuits (FIGS. 13, 15 and 16) are shown as being arranged outside of the motors 34, 34*a* and 34*b***.

Suitable motion limiting switches, as **46–47, 46*a*–47*a* and 46*b*–47*b*** are manufactured by General Electic Co. and are known as its JA Series 115 and Series JA 0102.

Suitable sanitary paper roll and supply means 59 may be mounted on each table cushion section 21–22–23, as shown in FIG. 3.

DETAILED DESCRIPTION OF THE OPERATION OF THE CHIROPRACTIC TABLE 15

The operation of the new chiropractic table is as follows: In order to position the table cushion sections 21–22–23 at the proper height or elevation to meet the needs of the doctor or his assistant, and to position the table cushion sections 21–22–23 all in coplanar relationship, as in full lines in FIG. 1, or out of coplanar relationship and at various different elevations to enable the doctor to treat advantageously and with facility various areas or sections of the patient's spine, the two groups of manually operable motor control toggle switches 56–57–58 or **56*a*–57*a*–58*a* (FIGS. 1, 13 and 14) may be selectively manipulated from either side of the table 15 to close the power supply circuits, as 49–49*a*–49*b*, to a corresponding one of the electrical operating motors 34–34*a*–34*b*, and to a corresponding one of the current directional flow control devices 68–69 or 70 embodied therein, thereby setting the selected operating motor 34 or 34*a* or 34*b*** in operation.

As the selected operating motor 34 or **34*a* or 34*b* is thus set in operation, power is delivered therefrom by way of its drive shaft 37 and the power transmitting means, in the form of the sprocket gear 36, sprocket chain 38, and sprocket gear 39 to the jack screw 32–30, thereby causing the jack screw 32–30 to rotate in and relative to the internally threaded jack screw tubular member 27–28 which is thereupon raised relative to the jack screw housing 25 and the jack screw 32–30. This upward motion of the tubular jack screw member 27–28 acts, through the platform 29, to raise the selected table cushion section, as 21, to the desired height to suit the needs of the doctor or his assistant, and the other table sections 22–23** may be similarly raised or lowered to desired elevations and positions.

The three power supply lines, as **74–75–76, 74*a*–75*a*–76*a* and 77*a*–77*b*–77*c* to the three (3) electrical operating motors 34–34*a*–34*b*, in conjunction with the current directional flow devices, as 68–69–70, embodied therein, in conjunction with the three pole double throw toggle switches, as 56–57–58 (FIGS. 1 and 13) or 56*a*–56*a*–58*a* (FIGS. 13 and 14) enable the direction of rotation of the three (3) reversible split phase electrical operating motors 34–34*a*–34*b*, shown in FIG. 13, to be manually controlled from either side of the table 15 so as to selectively raise or lower the table cushion sections 21–22–23**.

The three (3) pole, double throw toggle switches **56*b*–57*b*–58*b* (FIGS. 9 and 16) and related current flow directional devices similar to the current flow directional devices 68–69–70 and related parts, FIG. 13, enable all three (3) of the table cushion sections 21–22–23 to be raised or lowered simultaneously from either side of the table 15 by operation of the foot pedal controlled toggle switch control device shown in FIGS. 9 to 12, inclusive, and the operation of which is as follows: When the doctor or his assistant desires to raise or lower all three (3) of the table cushion sections 21–22–23, simultaneously, he may press downwardly by his foot on one of the foot pedals 79—79 or 80—80 so as to rotate the rock shaft 83 in either a clockwise or a counterclockwise direction, depending on whether he wishes to raise or lower the three table cushion sections 21–22–23 simultaneously. This rotational movement of the rock shaft 83 acts, through the sleeve 85 and the tubular switch operating members 86–87–88 attached thereto, to move the switch arms 89–90–91 of the three (3) toggle switches 56b–57b–58b simultaneously, against the action of the resetting coil springs 94—94, thereby closing the three (3) toggle switches 56b–57–b–58b and the electrical circuits, as 49–49a–49b, to the three electrical operating motors 34–34a–34b and to the current flow directional control devices, as 68–6–9–70 embodied therein, and the motion limiting switches, as 46 and 47, 46a and 47a and 48a and 48b (FIG. 13), thereby setting the three electrical operating motors 34–34a–34b in operation and in a direction of rotation such as to cause the three (3) table cushion sections 21–22–23 to be raised or lowered simultaneously depending upon the direction of movement imparted to the rock shaft 83 by foot pressure exerted on a selected one of the foot pedals 79—79 or 80—80.**

After the electrical operating motors 34–34a–34b have simultaneously raised or lowered all three (3) of the table cushion sections 21–22–23 to the desired height, the operating circuit to the motors 34–34a–34b (FIG. 13) is broken or opened by the corresponding motion limiting switches 46–47, 46a–47a and 48a–48b, whereupon the then tensioned resetting springs 94—94 (FIGS. 9 and 11) operate, through the center tubular switch operating member 87, the sleeve 85 and rock shaft 83 to return the switch operating arms or members 89–90–91 to their initial or open circuit position while, at the same time, rotating the rock shaft 83 and the foot pedals 79—79 and 80—80 thereon back to their normal or at rest position.

As the jack screws 32–30 and the tubular jack screw member 28–27 raise the selected tubular cushion section, as 21, in the manner described above, the actuating rod 44 for the motion limiting switches 46 and 47 is raised with the table cushion section 21 and at the extreme upper limit of its movement the striker arm 48 on the actuating rod member 44 engages and opens the first motion limiting switch 46, thereby breaking the power supply circuit 49 to the directional current flow control device, as 68, which is embodied in the electric operating motor, as 34, and thus preventing further upward movement of the table cushion sections, as 21. Similarly, when the table cushion section, as 21, is lowered, the striker arm 48 on the lower end portion of the actuating rod member 44 engages the second motion limiting switch 47 on the lower end portion of the jack screw housing 25 and thereby breaks the power supply circuit 49 to the electric operating motor 34 and this prevents further downward movement of the table cushion section 21. In this manner, damage to the new chiropractic table 15 and to the table cushion sections 21–22–23, and other parts of the new apparatus, by overrunning of the parts, is avoided. Similar raising and lowering devices and motion limiting switch arrangements are provided for each of the other two table cushion sections 22 and 23.

To reverse the direction of rotation of a selected one of the electric operating motors 34–34a–34b, and the corresponding one of the jack screws 24–24a–24b, a selected one of the three pole toggle switches 56–5–7–58 is manipulated to reverse the direction of rotation of the selected motors, as 34, thereby also reversing the direction of rotation of the power transmitting means, as 37–36–38–39, and the corresponding one of the jack screws 32–30–27–28.

As shown in FIGS. 13, 15 and 16, there are four (4) poles in each of the electric operating motors 34–3–4a–34b and there are a total of twelve electrical conductor wires leading into or out of the three (3) electrical operating motors 34–34a–34b.

Thus, FIG. 13 shows the electrical operating circuit for the three electrical operating motors 34–34a–34b which is under control of the first group of three (3) manually operable toggle switches 56–57–58 which are manually operable from the side of the table 15 shown in FIG. 1; FIG. 15 shows the corresponding electrical operating circuit for the three (3) electrical operating motors 34–34a–34b which is under control of the second group of three (3) manually operable toggle switches 56a–57a and 58a which are manually operable from the side of the table 15 opposite the side shown in FIG. 1, as partially shown in FIG. 14; and FIG. 16 shows the corresponding electrical operating circuit for the motors 34–34a–34b which is under the control of the foot pedal controlled toggle switches 56b–57b and 58b which are operable from either side of the table 15 under the control of the foot pedal-controlled toggle switches control device 78 (FIGS. 1 and 9 to 12, inclusive).

Thus, those parts of the electrical operating circuit shown in FIG. 15, which correspond to similar parts shown in FIG. 13, have, except where the parts are common to both FIGS. 13 and 15, been given the same reference numerals followed by the additional reference characters *c*, *d*, or *e*, and those parts in FIG. 16 which correspond to similar parts shown in FIG. 13, except where the parts are common to both FIGS. 13 and 16, have been given the same reference numerals followed by the additional reference characters *f*, *g* or *h*.

It will thus be seen from the foregoing description, considered in conjunction with the accompanying drawings, that the present invention provides a new and improved chiropractic table having the desirable advantages and characteristics and accomplishing its intended objects including those hereinbefore pointed out, and others which are inherent in the invention.

We claim:

1. A chiropractic table comprising:

a. a supporting base;
b. a table disposed above and supported by the said supporting base and adapted to support a patient thereon and including
   1. a plurality of separately and individually movable table cushion sections arranged in generally parallel horizontal relationship relative to each other but adapted to be lowered vertically into and out of generally horizontal coplanar relationship with each other;
c. individual raising and lowering means for vertically raising and lowering each of the said table cushion sections separately and individually relative to the other table cushion sections;
d. a plurality of individual electrical power means for individually operating each of the said raising and lowering means;
e. individual power transmitting means for delivering power from each of the said individual electrical power means to each of the said raising and lowering means;
f. individual electrical power supply means for supplying electrical power to each of the said individual electrical power means;
g. individual electrical power control means for individually controlling the operation of the said electrical power supply means and the said individual electrical power means;

h. first motion limiting means for limiting the upward movement of each of the said raising and lowering means and the said table cushion section mounted thereon;

i. second motion-limiting means for limiting the downward movement of each of the said raising and lowering means and the said table cushion section mounted thereon; and j. actuating means for actuating the said first motion-limiting means and the said second motion-limiting means at different elevations of each of the said table cushion sections.

2. A chiropractic table as defined in claim 1 which includes a. a vertically extending actuating member carried by and suspended from each of the said table cushion sections; and in which the said actuating member has thereon b. striker means for engaging and actuating the said first motion-limiting means and the said second motion-limiting means in the raised and lowered positions, respectively, of the said table cushion section and the said actuating member attached thereto.

3. A chiropractic table comprising:

a. a supporting base including 1. spaced side walls;

b. a table disposed above and supported by the said supporting base and adapted to support a patient thereon and including 1. a plurality of separately and individually movable table cushion sections arranged in generally parallel horizontal relationship relative to each other but adapted to be lowered vertically into and out of generally horizontal coplanar relationship with each other;

c. individual raising and lowering means for vertically raising and lowering each of the said table cushion sections separately and individually relative to the other table cushion sections;

d. a plurality of individual electrical power means for individually operating each of the said raising and lowering means;

e. individual power transmitting means for delivering power from each of the said individual electrical power means to each of the said raising and lowering means;

f. individual electrical power supply means for supplying electrical power to each of the said individual electrical power means;

g. individual electrical power control means for individually controlling the operation of the said electrical power supply means and the said individual electrical power means;

h. the said individual electrical power control means including 1. a plurality of switch means arranged at one side of the said supporting base for selectively operating each of the said individual electrical power means to selectively raise and lower each of the said table cushion sections individually;

2. a plurality of switch means arranged at the other side of the said supporting base for selectively operating each of the said individual power means from the said other side of the said supporting base so as to selectively raise or lower each of the said table cushion sections individually; and i. additional switch means for actuating all of the said power means simultaneously so as to raise or lower all of the said table cushion sections simultaneously.

4. A chiropractic table as defined in claim 3 which includes a. switch-operating means arranged at each side of the supporting base for operating said additional switch means so as to enable all of the said table cushion sections to be raised or lowered simultaneously from either side of the said supporting base.

5. A chiropractic table as defined in claim 4 in which the said switch-operating means is in the form of a. a foot pedal-operated control means arranged at each side of the said supporting base for operating the said additional switch means from either side of the said supporting base so as to raise or lower all of the said table cushion sections simultaneously from either side of the said supporting base.

6. A patient treatment table comprising:

a. a supporting base including 1. spaced side walls including a. a first side wall; and b. a second side wall;

b. a table disposed above and supported by the said supporting base and adapted to support a patient thereon and including 1. a plurality of separately and individually movable table cushion sections arranged in a preselected relationship relative to each other but adapted to be moved into and out of said preselected relationship with each other;

c. individual raising and lowering means for raising and lowering each of the said table cushion sections separately and individually relative to the other table cushion sections;

d. a plurality of individual electrical power means for individually operating each of the said raising and lowering means;

e. individual power transmitting means for delivering power from each of the said individual electrical power means to each of the said individual raising and lowering means;

f. individual electrical power supply means for supplying electrical power to each of the said individual electrical power means;

g. individual electrical power control means for individually conrolling the operation of the said electrical power supply means and the said individual electrical power means;

h. a plurality of switch means arranged at said first side of the said supporting base for selectively operating each of the said individual electrical power means to selectively move said table cushion sections individually into and out of said preselected relationship with each other; and i. additional switch means arranged at the said first side of said supporting base for actuating all of the said power means simultaneously so as to move said table cushion sections simultaneously into and out of said preselected relationship.

7. A patient treatment table as defined in claim 6 which includes a. plurality of switch means arranged at the second side wall of the said supporting base for selectively operating each of the said individual power means from the said second side of the said supporting base so as to selectively move the said table cushion sections individually into and out of the said preselected relationship with each other.

8. A patient treatment table as defined in claim 7 which includes a. switch-operating means arranged at each of said side walls of the said supporting base for operating the said additional switch means so as to enable all of said table cushion sections to be moved simultaneously from either the said first side wall or the said second side wall of the said supporting base.

9. A patient treatment table as defined in claim 8 in which said switch-operating means is in the form of a. foot pedal-operating control means arranged at each of the said first and second walls of the said supporting base for operating the said additional switch means from either side of the said supporting base so as to move all of the said table cushion sections simultaneously into and out of said preselected relationship from either side of the said supporting base.

* * * * *